United States Patent [19]

Conrad et al.

[11] Patent Number: 4,845,653
[45] Date of Patent: Jul. 4, 1989

[54] METHOD OF DISPLAYING MULTI-PARAMETER DATA SETS TO AID IN THE ANALYSIS OF DATA CHARACTERISTICS

[75] Inventors: Morgan P. Conrad, Mountain View; Thomas A. Reichert, Los Altos, both of Calif.; James C. Bezdek, Lexington, S.C.

[73] Assignee: Becton, Dickinson and Company, Franklin Lakes, N.J.

[21] Appl. No.: 46,619

[22] Filed: May 7, 1987

[51] Int. Cl.[4] .............................................. G06F 3/037
[52] U.S. Cl. ...................................... 364/521; 340/747
[58] Field of Search ............... 364/172, 194, 415, 497, 364/521, 554, 555, 413.1, 510, 413.08, 526; 340/747

[56] References Cited

U.S. PATENT DOCUMENTS

| | | | |
|---|---|---|---|
| 3,976,862 | 8/1976 | Curbelo | 364/555 X |
| 4,045,655 | 8/1977 | Suzuki et al. | 364/415 X |
| 4,527,240 | 7/1985 | Kvitash | 364/415 |
| 4,661,913 | 4/1987 | Wu et al. | 364/555 X |

Primary Examiner—Gary V. Harkcom
Assistant Examiner—Mark K. Zimmerman
Attorney, Agent, or Firm—Richard J. Rodrick

[57] ABSTRACT

The method involves displaying at least three different parameters of particle-related data in multiple two-parameter data fields on a screen for viewing by a user. A position variable cursor is applied to any two-parameter data field and a region of data events is created within the data field by the cursor. Data events in the created region are linked and corresponding data events, defined by all other parameter data fields displayed on the screen, are then located. This method includes visually differentiating the data events in the other data fields which correspond to the data events in the created region of the first data field. This differentiation permits the user to identify these same data events on all of the two-parameter data fields to thereby facilitate visual exploratory data analysis.

30 Claims, 7 Drawing Sheets

METHOD OF DISPLAYING MULTI-PARAMETER DATA SETS TO AID IN THE ANALYSIS OF DATA CHARACTERISTICS

BACKGROUND OF THE INVENTION

1. Field of the Invention.

The present invention relates to a method for making multi-parameter data, and more particularly, concerns a method for making multi-parameter data of dimensionality greater than two viewable by a human analyst on a screen to determine one or more characteristics of cells or other particles of interest.

2. Background Description.

Flow analysis of cells or particles has been relied upon to determine different characteristics of individual particles. Flow cytometry generally refers to those techniques in which cells or other biological particles are caused to flow in a liquid stream, substantially one at a time, so that certain characteristics thereof may be measured, sensed or detected. For example, a liquid sample containing cells is typically directed through a flow cytometry apparatus in a rapidly moving liquid stream so that each cell passes serially, and substantially individually, through a sensing region. As each cell passes through the sensing region, different characteristics of the cell may be determined or detected. If, for example, an incident beam of light is directed into the sensing region, the passing cells scatter such light as they pass therethrough. Further, fluorescence is emitted by autofluorescent or labeled cells which have been excited as a result of passing through the excitation energy of the incident light beam. Light scatter and fluorescence related to these passing cells may be detected to provide various information about the properties or characteristics of those cells.

In addition to emitted or scattered light, other physical or chemical properties of each cell may be detected. For example, light absorbance may be measured as each cell passes through the incident light beam, and electronic cell volume may be measured by using the well-known Coulter principle in which the impedance measurement of a cell passing through an orifice is related to cell volume. These analyses are most useful in areas of research, immunology, hematology and the like. The researcher, for instance, may be interested in determining specific characteristics of individual cells so that the cells may be classified, identified, quantified and perhaps sorted for further investigations or analysis.

Advances in flow cytometry instruments have made the acquisition of multi-parameter data relatively straightforward. Commercially available flow cytometry instruments provide features for the acquisition of simultaneous data including four, five or six different parameters related to each cell under analysis. While some of these data are displayed on a screen to a user in real-time format during the data collection procedures, the data may also be stored in its entirety, in what is called list mode, for further analysis or refinement. With so much information available, multi-parameter or multi-variate analysis of the data may take on a complexity that could render meaningful analysis difficult. Accordingly, different techniques have evolved to make the data handling aspects of flow cytometry analysis not only more meaningful, but also more convenient and simplified for the user.

For example, "gating" techniques have been employed in the visual presentation of data on the CRT screen used in accompaniment to flow cytometers for visualization by the user. In this well-known and utilized technique, only those cells having values for the measured parameters falling within set limits, the gated values, may be seen on the screen. Those cells which fall outside of the gated values are usually eliminated from view so that they vanish from the screen. Of course, this technique simplifies or clarifies the data events displayed on the screen to make it easier for the viewer to study the selected cells of interest. To reintroduce the eliminated cells onto the screen for viewing, extra steps are involved; the user normally will not be able to view the gated events at the same time that the non-gated data events are on the screen.

A more sophisticated version of gating, referred to as window trace integration, was recently described by Kachel, in "Interactive Multi-Window Integration of Two-Parameter Flow Cytometric Data Fields," *Cytometry* 7:89-92 (1986). In the window trace integration, a cursor point on the screen may be moved by the user over the structures of a two-parameter field leaving a trace on the screen. The window is that field selected by the trace for integration. In the Kachel technique, the trace left by the cursor point is shown with intensified brightness in the ground plane of the two-parameter field. Up to eight independent window traces may be performed on the single two-parameter field, as described by Kachel. In addition to window trace integration, Kachel also describes another technique, referred to as painted field integration, for identifying a field of interest for those cells under analysis in the two-parameter field. In the painted field technique, the cursor point may be used as a brush for "painting" the field so that each channel of the two-parameter field touched by the cursor is marked as part of the integration window. In addition, Kachel describes window trace painting in which the painting may be performed by moving the entire window trace generated by using cursor point painting.

The techniques described by Kachel are indicative of the new approaches for handling two-parameter data for the analysis of cells, particularly with respect to flow cytometric data. The goal is provide the user with the ability to quickly and efficiently discriminate different kinds of cells. However, even though the approach described by Kachel represents an advance in the handling of flow cytometric data, it is limited to a single two dimensional display and does not provide any insight into multi-parameter, multi-dimensional data. It is to a visualization of data of dimensionality greater than two and the achievement of the aforementioned goal of allowing the user to more efficiently and conveniently discriminate cells and cell characteristics, that the present invention is directed.

SUMMARY OF THE INVENTION

The method of the present invention for analyzing multi-parameter data comprises displaying at least three different parameters of particle-related data in multiple two-parameter data fields on a screen for viewing by a user. A position-variable cursor is applied to a any chosen two-parameter data field and a region is created on that data field by use of the cursor. The created region is linked to all data events within that region, and corresponding data events are then delineated, identified or found on all other two-parameter data fields on the screen. The method includes visually differentiating the created region, the data events contained therein and those in the other data fields corresponding to the events in the created region of the first data field. Accordingly, the user may identify the linked data events on all of the two-parameter data fields displayed on the screen which correspond with each other.

In a preferred embodiment of the present invention, a method for analyzing multi-parameter flow cytometric data permits the determination of cells possessing one or more characteristics. A plurality of two-parameter data fields is displayed on a screen for viewing by the user. These fields represent different displays of at least three-parameters relating to characteristics of cells. A position variable cursor is applied to any one of the data fields and the cursor is moved to enclose selective data events in a defined region. Data events in the region defined by movement of the cursor are linked with corresponding events defined by different parameters in the remaining data fields on the screen. Linking is achieved through the multi-parameter data related to the cells stored in memory after having been obtained by flow cytometric procedures. Each data event found in the defined region is correspondingly delineated in the remaining data fields, but identified by the different parameters thereof. Data events corresponding to the events in the defined region and delineated in the remaining data fields are visually differentiated on the screen. This differentiation is achieved by causing the data events in the created region and the corresponding data events in the remaining data fields to have a color, intensity or blink frequency different from data events not included in the region. In this regard, the user may identify the linked data events which correspond with each other on all of the two-parameter data fields, displayed for purposes of cellular analysis.

In accordance with the principles of the present invention, a number of advantageous features are provided to achieve the goals set forth above. In particular, multi-parameter, as distinct from two-parameter, data analysis is facilitated and made more convenient for the user. This invention offers quick and rapid displays of specific data events relating to cell types or cell subpopulations. The speed and interactive nature of the invention permits the user to conveniently and naturally visualize and differentiate cell subpopulations in complex samples in multi-parameter space. Data events, representing different cell types or cell subpopulations, are visually differentiated by a change of brightness qualities on the screen, blinking or flashing events or color differences. Indeed, a multiplicity of colors may be chosen to distinguish different cells or cell subpopulations. When the user selects a region of cells on one of the displays on the screen, all selected subpopulations corresponding to that region are shown at once on all remaining displays on which these subpopulations are represented by different cell parameters. Since all selected subpopulations are visualized at the same time, the relative positions of the data events are easily determined.

In addition, movement of the cursor for selecting regions or areas of interest on a display is preferably controlled by a hand-manipulated mouse electrically connected to the computer/display console. Use of this mouse for cursor movement readily permits the user to "paint" those regions on the display selected for identification or analysis. Alternatively, since a point cursor in any particular display corresponds to a line or region in any other display, small movements of such a cursor allow instantaneous exploration of the correspondence of subpopulations and regions of potential interest to the analyst. A further feature of the present invention allows the user to erase or reverse the selection of regions of interest on the display so that all or part of the region can be made smaller than the region originally defined. This invention allows the user to more rapidly discriminate different types of cells or cell subpopulations than may be achieved by using presently existing techniques.

Use of painted gates is also advantageous for subsequent or future analysis of the multi-parameter data, and is particularly beneficial for the sorting of particles or cells on a physical acquisition basis.

DETAILED DESCRIPTION

Figure 1:
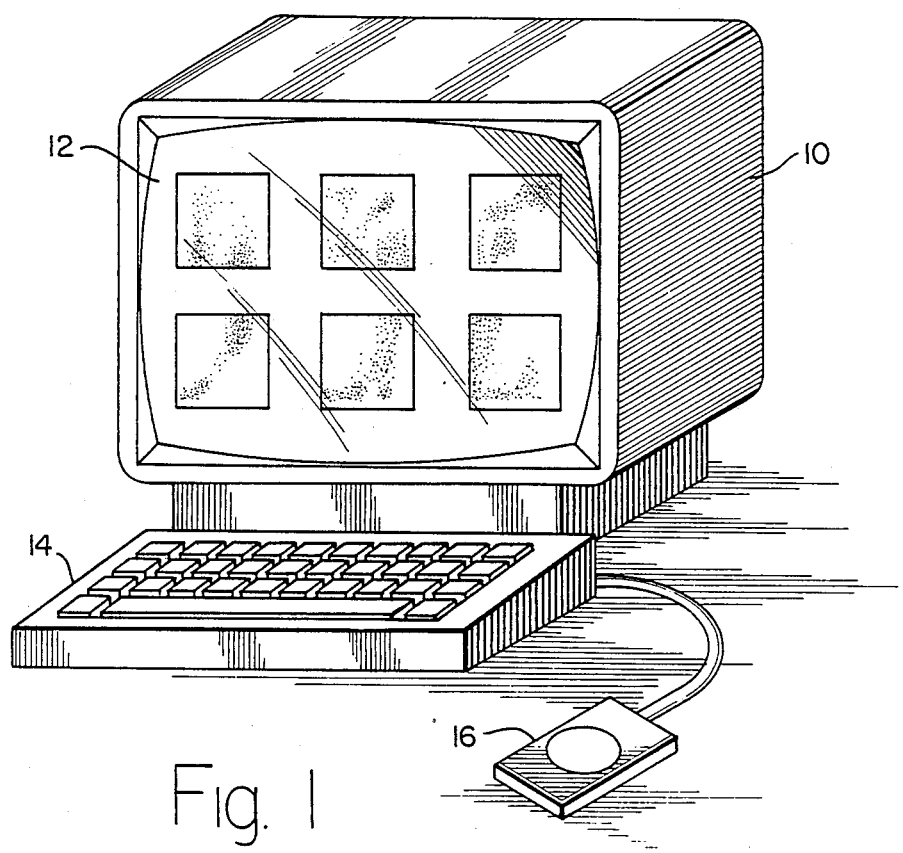
FIG. 1 is a perspective view of an embodiment of a computer console and display screen useful for carrying out the method of the present invention for analyzing multi-parameter data.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

It is understood that the present invention is useful for analyzing multi-parameter data of any form, including continuous-, discrete- and categorical-valued data. Any multi-parameter data set may be so analyzed, including, but not limited to, data obtained by pattern discovery or cluster analysis techniques, image processing, image cytometry and the like. The present invention is especially useful and suitable for analyzing such data as that obtained by flow cytometric procedures. As mentioned above, there are flow cytometer instruments available on the commercial market which permit the user to obtain multi-parameter data with respect to cells or biological particles to be analyzed. Two such flow cytometer instruments are available from Becton Dickinson Immunocytometry Systems, Mountain View, Calif. One of these instruments is sold as the FACScan ™ analyzer and is utilized for cellular analysis purposes; another such instrument is known as the FACStar ™ cell sorter which not only analyzes cells, but also sorts the cells into different groupings. For purposes of exemplary description only, the present invention will be explained in conjunction with the functions of a flow cytometry instrument.

In flow cytometry instruments, such as mentioned above, it is known how to obtain four simultaneous signals with respect to each cell passing through the sensing region. For instance, two light scatter signals may be detected, such as forward scatter (FSC) and side scatter (SSC) preferably at right angles or 90° with respect to the incident light beam. In addition, two different fluorescence signals may be detected with respect to the surface or intracytoplasmic characteristics of each cell passing through the flow cytometer. Thus, four different data signals may be obtained about each cell passing through the flow cytometer instrument. These data are normally observed in a two-dimensional perspect, on a screen as the information is being collected, and then stored in a format appropriate for subsequent access and analysis. It is understood that, while the collection of four-parameter data has been specifically mentioned above, it is merely for exemplary purposes only and should not be construed to be limitative of the scope of the instant invention.

Having obtained and stored the data about the cell sample under analysis, different formatting techniques may be employed to analyze the data. Use of computer programs, microprocessors and display consoles is common and well-known for the refinement or analysis of flow cytometric data. As seen in FIG. 1, a monitor 10 is provided for displaying the data on a CRT screen 12 for visualization by the person undertaking the analysis. A keyboard 14 permits the user to access the data in the format chosen to store the data. In the embodiment illustrated, a mouse 16 is preferably included so that the cursor, as described below, applied to screen 12 may be electronically moved across the screen by hand manipulation of the mouse by the user, in a fashion well-known to those skilled in the art.

It is appreciated that the data obtained by the flow cytometric techniques may be displayed or formatted in many different forms, as may be desirable or feasible for the type of analysis contemplated. The computer program or algorithm may be devised to show the data in graphs, charts and, preferably, for purposes of the present invention, in different color schemes (it being assumed that monitor 10 has color capabilities). As mentioned above, one of the goals of the present invention is to provide a rapid and convenient tool for the user to discriminate different cell types or cell subpopulations in complex samples in multi-parameter space. To this end, a goal of the present invention is to present multiple views, for example, six, of the flow cytometric data at the same time so that the user may visualize the different displays all on the same screen. In this display of multiple data fields as contemplated herein, cell type or cell subpopulation differentiation is to be provided either directly by the user or by pattern recognition or cluster analysis or other heuristic or mathematical techniques so that it is possible to analyze, detect or identify such differentiated cells in a single viewing of the display screen. It should be noted, however, that the present invention is not limited to viewing data on a single screen, since there are instances when all the desired data may not fit on a single screen. Multiple screens may be used or linked for the simultaneous display of large amounts of data. Alternatively, one screen may be programmed to display data of different types on a sequential or rotating basis, if desired or necessary.

Figure 2:
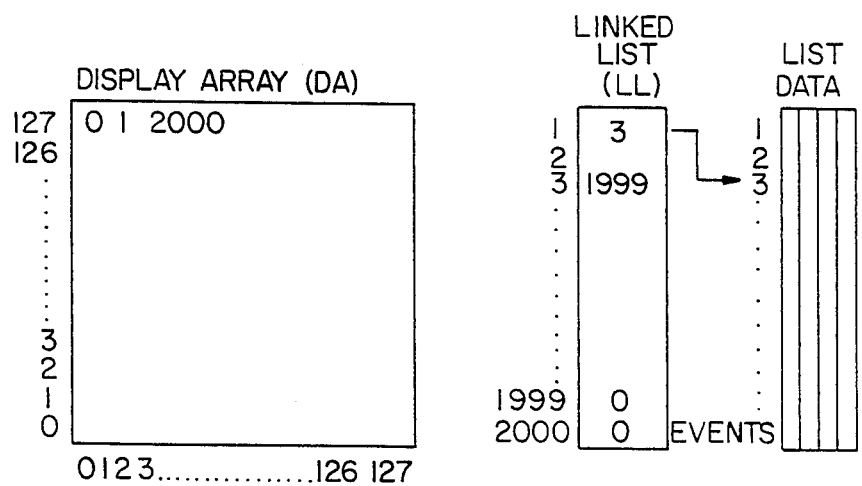
FIG. 2 is a schematic representation of a matrix array illustrating in simplified form the general functions of the computer program/algorithm under which the method of the present invention operates.

In the computer program to be generally described below, the flow cytometric data includes four parameters namely forward scatter (FSC), side scatter (SSC), fluorescence 1 (FL1) and fluorescence 2 (FL2). These four different parameters are to be displayed in six different two-parameter display fields on the display screen 12 at the same time. Furthermore, a linkage between all regions and subregions delineated on the display fields and the cells which fall within those regions is provided so that corresponding data events within those regions may be identified with respect to all the measured parameters, in this example, four. A generalized and schematic representation of the computer program for such a display format is shown in FIG. 2.

It can be seen that an array (called "Display Array" in FIG. 2) is set up for each display of a data field (here, $128 \times 128$ in dimension). The entries in this array point to an event (if any) which lies within the correspondent region of the data field. These entries are then used as indices into the linked list for all events which have parameter values which permit display in that data field. The measured parameters and other properties of the cells, such as color assigned, are stored in and obtained from sources such as tables and permit each cell to be displayed on all data fields using the appropriate parameters. An important realization is that the events need not come from the same data file or even from the same experiment or sample, since the link may contain information about the experiment.

Figure 3:
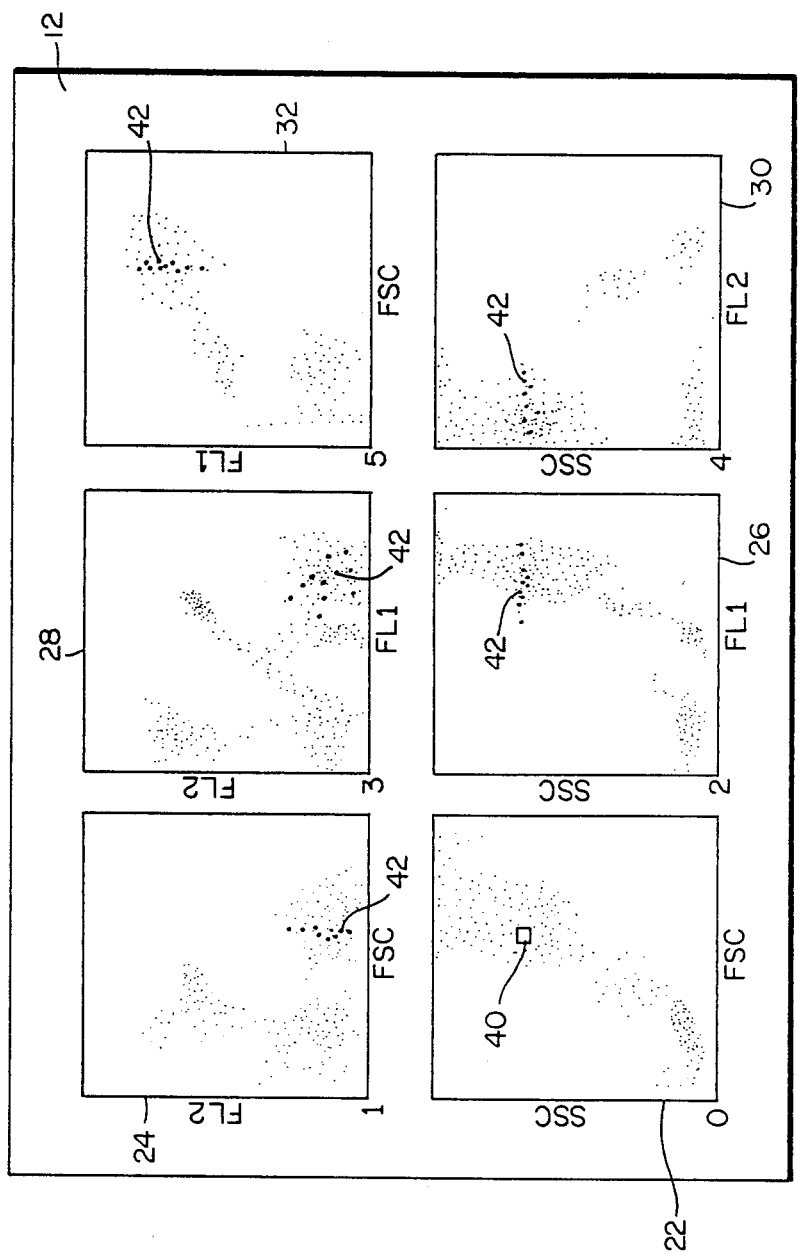
FIG. 3 is an illustration of the display screen simultaneously showing six two-parameter data fields covering four different parameters related to cells under analysis, and further illustrating the cursor for creating a defined region in one of the data fields and the corresponding data events in the remaining data fields.

Turning now to FIG. 3, a representative display of the preferred formatting approach of the present invention is seen on CRT screen 12 of the monitor. In this embodiment, there are six two-parameter data fields shown at the same time on screen 12. For ease of viewing, each data field is preferably, but not necessarily, enclosed within a box with labelled axes so as to provide better definition for the user. In this format, each data field is preferably a dot plot representation of the data events of the four different parameters obtained by flow cytometric procedures, and stored in memory for subsequent analysis. Data field 22 is a two-parameter plot of SSC and FSC; data field 24 is a plot of FL2 and FSC; data field 26 is a plot of SSC and FL1; data field 28 is a plot of FL2 and FL1; data field 30 is a plot of SSC and FL2; and data field 32 is a plot of FL1 and FSC.

When the user calls up the flow cytometric data for viewing in the format of FIG. 3, the data appears on the respective fields preferably as gray dots. The dots may be individually evident, or the dots may appear as clusters. The locations of the dots on certain two-parameter fields indicates to the viewer that certain cell types or even cell subpopulations are present in the sample. For instance, the immunologist may identify different subsets of leukocytes in one or more data fields by noting the location of the clusters of dots; one cluster of dots may represent lymphocytes, another, monocytes and a third cluster, granulocytes. Since all of the data obtained with respect to the cells is displayed, one purpose of the present invention is to provide additional refinement of that data without using the old, known gating techniques which provide windows for keeping the data events on the screen, while eliminating from the screen those data events which fall outside of the gated values for the measured or calculated parameters.

In the instant technique, the computer program provides for the application of a cursor 40 to any one of the two-parameter data fields illustrated on screen 12, the choice being afforded to the user according to the computer program controls. In the embodiment illustrated, cursor 40 is shown on data field 22 as a small square box. Cursor 40 may be moved in any direction on the data field either by use of keys on control panel 14 or, preferably, by use of the hand-manipulable mouse 16. To the viewer, cursor 40 appears as a bright box, whose size may be varied either to make it smaller or larger, again by virtue of controls provided in the program. Further, for ease of identification of the cursor, it is preferred that the cursor blink or flash intermittently so that it may be readily discerned.

Wherever the cursor is placed on a particular data field, its purpose is to touch or cover data events or dots. Thus, whatever the size of cursor 40, a region of coverage is provided within the boundaries of the box-configuration of the cursor. All those dots or data events touched by cursor 40 are marked or designated as part of a painted field or integration window. Insofar as cursor 40 may be interactively moved over the entire two-parameter data field, the user may select any portion or region of data events for a concentrated or refined analysis.

Once the user positions cursor 40 over a region of dots on data field 22, the linked list of data events, as described above with respect to the program outline of FIG. 2, accesses all the data events which are at that location on data field 22. As a result, the corresponding data events, defined on the remaining two-parameter fields on the screen, are identified for the viewer. Identification of the data events in data fields 24,26,28,30 and 32 occur as dots which are brighter on the respective data fields, or as flashing/blinking dots. Thus, all those data events touched by cursor 40 in data field 22 and represented there by two parameters may now be visualized in different formats, at the same time, so that four-parameter analysis may be accomplished simultaneously on a single screen. For example, in data field 24, a series of bright or flashing dots 42 (illustrated as small circles for purposes of clarity) inform the user that these data events, identified by parameters of FL2 and FSC, correspond to the data events identified by parameters of SSC and FSC and touched by cursor 40 in data field 22. Similarly, bright or flashing dots 42 may appear in data fields 26,28,30 and 32. The quantity and location of dots 42 in the remaining data fields (other than the data field selected for application of the cursor) may provide information instructive to the user in analyzing or refining the originally obtained flow cytometric data. Ready and fast discrimination of cells or cell subpopulations is thus made available to the user by virtue of the multiple views of complex multi-parameter data.

Linkage of the corresponding data events from data field to data field facilitates the observation of multi-parameter data events with respect to each cell under analysis. In conjunction with the computer program outlined with respect to FIG. 2 above, all of the data events in the region covered by the cursor are electrically accessed and an electrical signal is directed to each other data field on the screen. These signals are related to a linked list of the multi-parameter data stored in memory after having been obtained by flow cytometric procedures. Accordingly, each data event found in the region touched by cursor 40 is correspondingly located in the remaining data fields on the screen, but is identified by the different parameters of each other two-parameter data field. This provides the user the opportunity to simultaneously visualize the quantitative, qualitative and location characteristics of the cells under analysis so that refinement of the data may be achieved. However, in a broader sense, events found in the region touched by the cursor do not have to be linked to events located in the remaining data fields. In working with data from different samples, files or experiments, the events, themselves, may be different. Such different events are linked only through the commonly demarcated region. Accordingly, the present invention permits the region, for example the region touched by the cursor, to be linked to different events from other files or samples which have a common region on one display.

Figure 4:
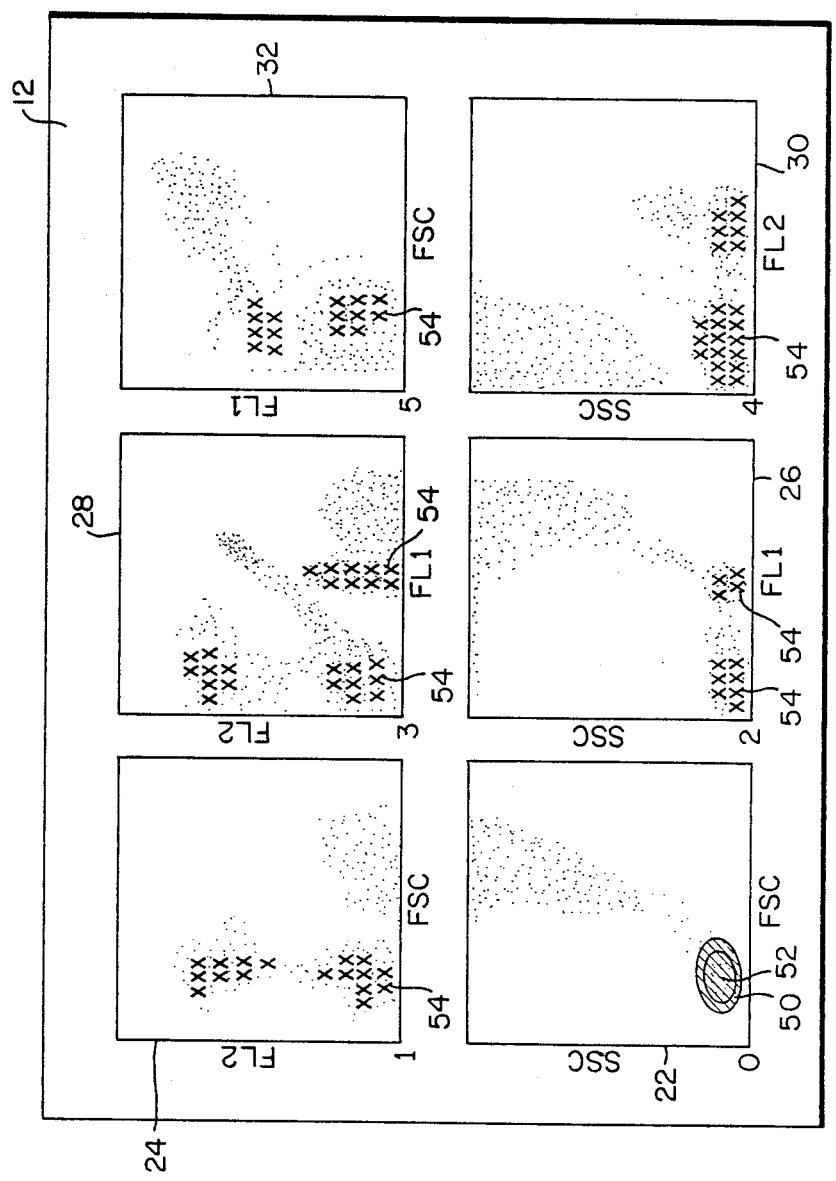
FIG. 4 is an illustration of the display screen showing the same arrangement as in FIG. 3, except that the cursor has been utilized to paint a region of interest with a different color to identify cells of interest.

Further flexibility of the instant invention may be seen by turning to FIG. 4. The same six data fields, as seen in FIG. 3, are simultaneously viewed by the user. However, instead of viewing only those cells within the current cursor box, the user may use the cursor to trace a region or to form an enclosure of data events. While conceptually the cursor is a point used to outline or "lasso" a region, in practice it is still a box or a "fat point." Also, the user does not have to form an enclosure, but may employ direct painting, especially for smaller regions, in a fashion somewhat similar to the technique described by Kachel. As seen on data field 22, a trace 50 has been made with the cursor (originally appearing as a point source). In a fashion similar to that described with respect to FIG. 3, the cursor is caused to appear on any data field, in this instance, data field 22. The cursor may be interactively moved in conjunction with hand manipulation of mouse 16, as seen in FIG. 1. Continued movement of the mouse permits the user to trace any shape configuration which is desired on data field 22 so that a region 52 is enclosed within the tracing. All those data events or dots covered by trace 50 or enclosed within the region are marked or identified in accordance with the linked list of data events, as described above. Thus, all the data events within region 52 are "touched" by the cursor for identification purposes, the computer program permits the user to cause region 52 to be "filled" in. In such case, all data events within region 52 may appear as brighter or as flashing/blinking events. This filling in procedure may be performed automatically, or the user may manipulate mouse 16 so as to move the cursor back and forth on data field 22 in brush-like fashion to manually paint the area or region to be filled in. It is the literal touching of the data events by the control cursor which causes the linked list to identify those touched data events for visual discrimination.

While region 52 may appear as brightened or flashing dots (completely filled in), it is preferred that the visual differentiation or discrimination be achieved with the addition of color to the region. Thus, and assuming console 10 has color capabilities, when the region has been selected by the user, traced and filled in, an appropriate button on control panel 14 may be pushed to instruct that the region to appear as a color different from those data events outside of region 52 on data field 22. Any color may be chosen, but for exemplary purposes of the instant invention, it will be assumed that region 52 is colored red. In a fashion similar to the display described in conjunction with FIG. 3, the linked list of the computer program accesses all corresponding data events in the other data fields appearing on display screen 12. Access to these corresponding data events in the other data fields carries with it the color-coding of the identified data events within region 52 of data field 22. Accordingly, all corresponding data events in remaining data fields 24,26,28,30 and 32 appear on the screen as red dots 54, either individually or in clusters (red dots 54 are designated by small "x's" in FIG. 4 to indicate that these dots are colored differently from the other dots on the screen). The color differentiation of the data events makes it easier for the viewer to visually identify and discriminate the cells under analysis.

Figure 5:
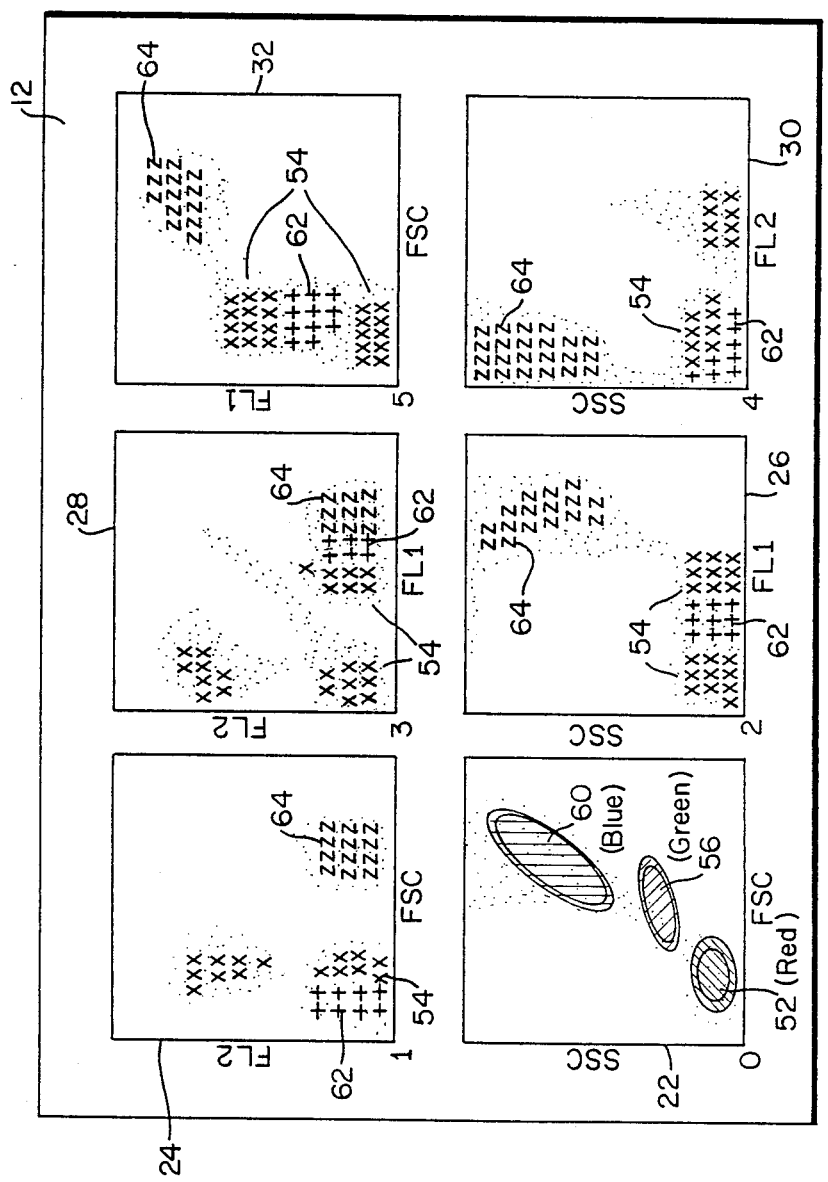
FIG. 5 illustrates the display screen with the same configuration as in FIG. 4 except that one of the data fields has been painted with three different colors to further discriminate the different cells in all of the data fields displayed.

Multiple regions or areas of the data field may be traced or painted with the cursor for color differentiation. FIG. 5 shows this embodiment. It can be seen in data field 22 of FIG. 5 that three regions 52,56 and 60 have been traced or painted thereon. Each region is programmed to present a different color to the user, for example, region 52 being red, 56 being green and region 60 being blue. All corresponding data events in the remaining data fields on the screen are identified through the linked list and appear as colored dots with the same color corresponding to the respective region of data field 22. Thus, in data fields 24,26,28,30 and 32, red dots 54 are designated by small "x's" as described above. All those data events corresponding to green region 56 on data field 22 appear as green dots 62 in the remaining data fields (green dots 62 are designated by "+" signs so as to indicate that these dots are colored differently from the other dots on the respective screens). In like fashion, data events corresponding to the blue data events of region 60 appear as blue dots 64 in the other data fields on the screen (designated by small "z's" to indicate that these blue dots are colored differently from the other dots on the data fields). Thus, the different colors provide a ready and easy visual differentiation of multiple regions of cells so that, for multi-parameter analysis, quantitative, qualitative and position-based evaluations may be preformed by the person analyzing the data.

While data field 22 of FIG. 5 illustrates three distinct color regions designated by numerals 52,56, and 60, it is appreciated that the different color regions do not have to be separated or discontinuous, as shown. Rather, the different color regions may overlap so that one or more data events may have a combination of colors. For example, if the three colors of red, blue and green are used to color data events, some dots may appear as yellow (red/green) other dots as cyan (blue/green) and other dots as violet (red/blue). If all three colors are associated with data events, the combined color appears as white. Therefore, if three initial colors are chosen to select different regions of data events, a total of seven different color combinations may be viewed by the user in the discrimination of cell types or cell subpopulations or other characteristics thereof. Of course, it is understood that the three color combinations just described are exemplary only, since fewer or greater than three colors may be employed in the color schemes contemplated by the present invention.

Another advantageous feature and part of the flexibility of the instant invention is the ability to erase or reverse the region of data events created on any data field with the cursor. For example, and referring to region 52 of FIGS. 4 or 5, the originally created region may be made smaller or larger after the analysis on the display has begun. Of course, to make the region larger, the user need only move the cursor to capture more data events with the proper command signals and use of the control panel. On the other hand, a reversal of the functioning of the cursor permits region 52 to be made smaller. This erasure or reversal is achieved by implementation of the computer program and use of the control panel to provide the eraser function. The cursor is then moved, preferably by manipulation of mouse 16, and each data event or dot which the cursor touches, in this mode, is decoupled or unlinked from the identified region of interest. If color is being used, all those data events which are erased have the color removed. If the data events are blinking or exhibited as brighter dots, the erasing function eliminates the blinking or brightness so that the data events appear as normal dots on the respective data fields, without being highlighted. Once again, this erasure feature is most convenient for the user since there need be no changing of display screens or the presentation of the original data into a different format. The interactive nature of the cursor along with the proper programming allows the user to perform a variety of manipulations on the displayed data. Of course, when erasure occurs in the created region of data field 22, the erasure is also linked to the corresponding data events in all of the other data fields on the screen.

Figure 6:
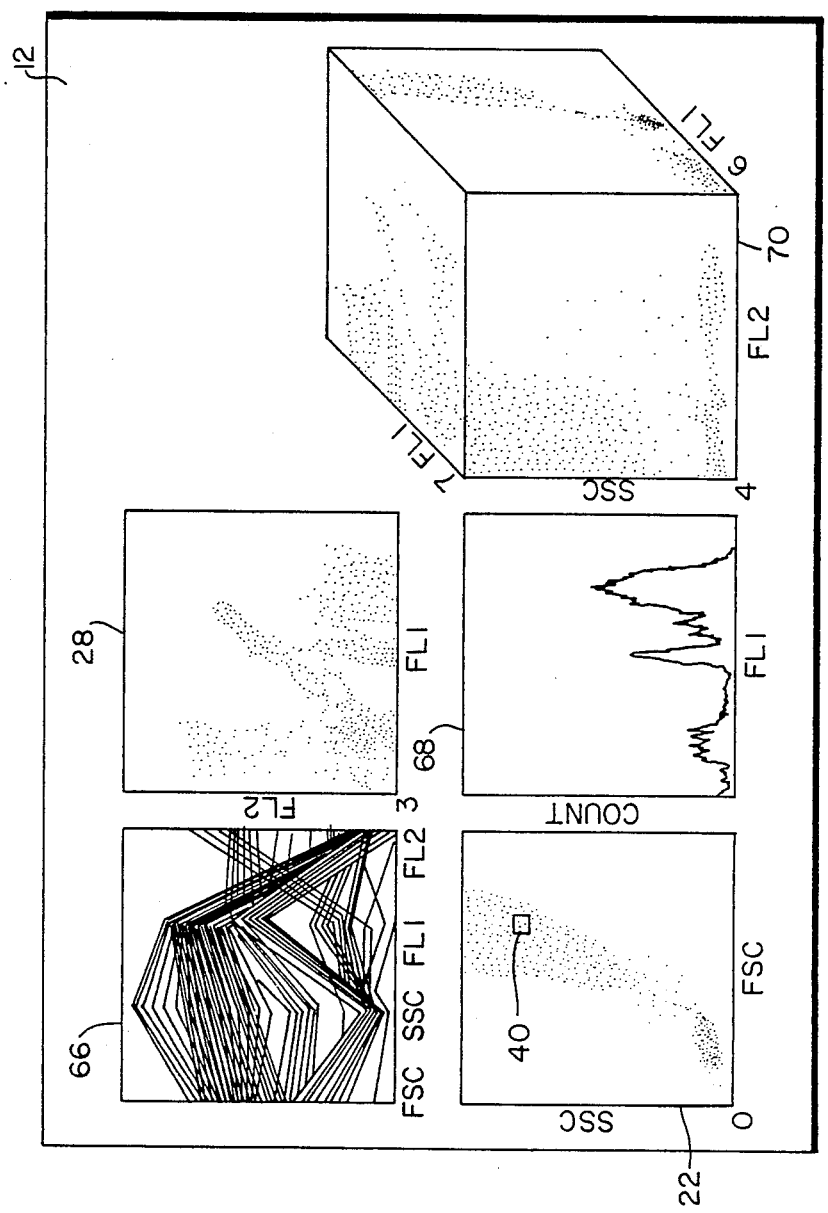
FIG. 6 is an illustration of the display screen similar to the previously illustrated display screens except that different data fields are displayed, including dot plots, a histogram, an N-plot and a cubical configuration.

Although FIGS. 3,4 and 5 have data fields in a dot plot configuration for the two parameters of each data field, other types of data displays or data fields are within the purview of the instant invention. FIG. 6 illustrates one variation which may appear on screen 12 to show a combination of different data fields at the same time. In this presentation, data fields 22 and 28 are the same as in the previously described displays. However, data field 66 has been substituted for data field 24. Data field 66 is referred to as an N-plot and places the four different parameters of forward scatter, side scatter, fluorescence 1 and fluorescence 2 on the X axis. The distribution of data events in the different channels of the array are displayed as functions of the four different parameters. This type of display provides the user with an additional way to characterize the data for analysis purposes. N-plots are described by Gray, J. W. and Dean, P. N., in "Display and Analysis of Flow Cytometric Data," *Am. Rev. Biophys. Bioeng.*, 9:509–539 (1980) and an illustration of the use of N-plots in cluster analysis is found in Murphy, R. F., in "Automated Identification of Subpopulations in Flow Cytometric List Mode Data Using Cluster Analysis," *Cytometry*, 6:302–309 (1985).

Data field 68 of FIG. 6 is substituted for data field 26 and is displayed in histogram form. In this particular data field, the count of events is displayed as a function of fluorescence (FL1). Histograms of the other parameters may also be displayed. Data field 70 is represented in cubical form so that three parameters may be visualized, namely side scatter (SSC), fluorescence 1 (FL1) and fluorescence 2 (FL2). Data field 70 is essentially a combination of the same information shown on the three separate data fields 26,28 and 30 of FIGS. 3,4 or 5. As in the previously described displays, cursor 40 may be applied to any data field on the display, and be moved thereabout, in order to identify those data events for analysis. It is appreciated that many other data field configurations, including the number of data fields displayed, may be used in conjunction with the present invention.

Figure 7:
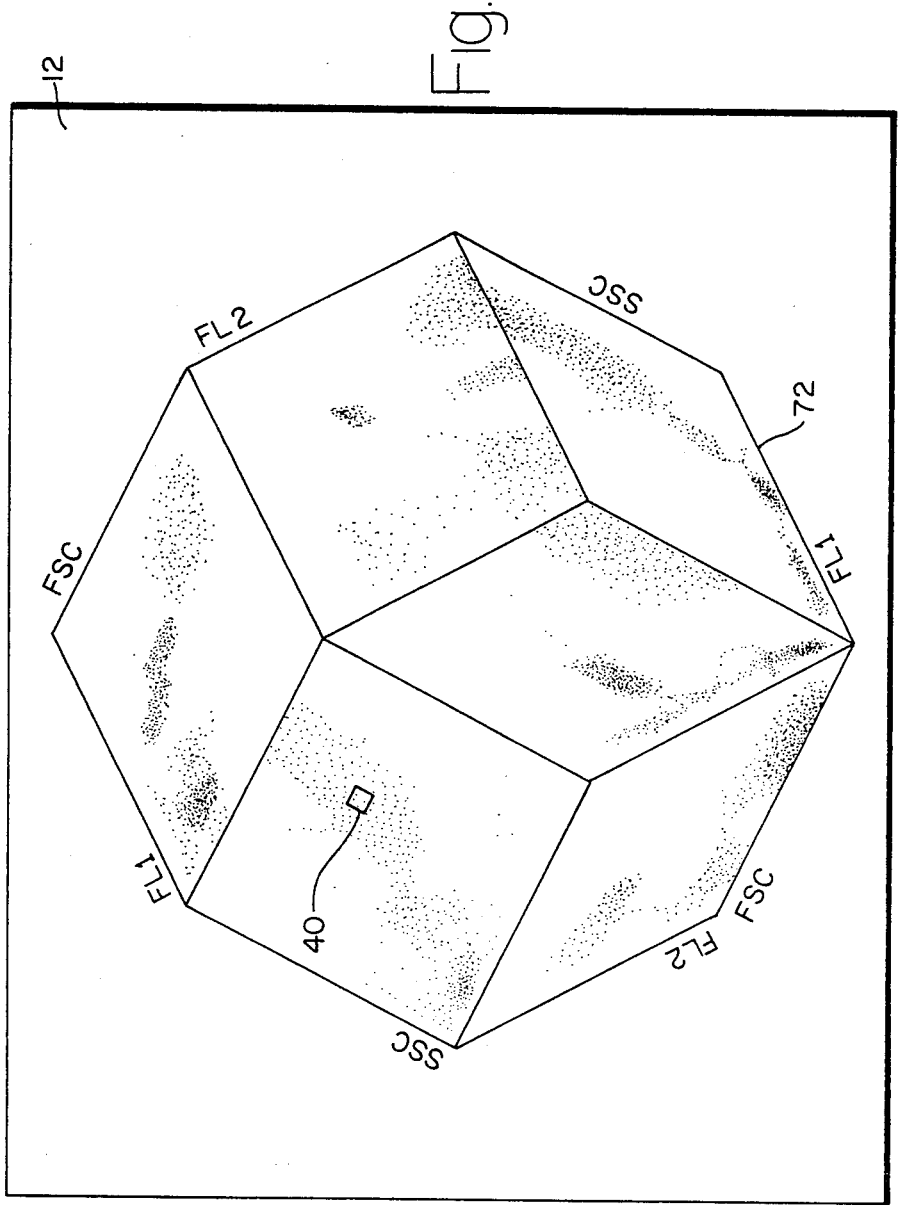
FIG. 7 illustrates a display screen in which there is a single graphical configuration (the "diamond" view) showing the relationship of four different parameters of the cells under analysis.

One such other data field is illustrated in FIG. 7. Instead of a plurality of separate data fields, each orthogonally presenting a two-parameter display, as in FIGS. 3, 4 or 5, all four parameters of side scatter, forward scatter, fluorescence 1 and fluorescence 2 may be presented in a single graphical configuration 72. In this diamond-like configuration, all parallel axes carry the same parameter. In this configuration, there are four sets of parallel axes for the four different parameters. Cursor 40 is applied to any data field represented by two parameters, similar to the previously described displays. All those data events covered by cursor 40, either within the cursor box or the traced or painted region, are identified by brightness qualities, flashing/blinking dots or color differentiation. All data events in the remaining two-parameter data fields within the single configuration are linked as in the previous embodiments so that these corresponding data events may be differentiated on all the remaining two-parameter fields throughout the graphical display. Other shapes, configurations or displays may be utilized, depending upon the choice of the operator and the ability of the computer program to permit such graphical variations. The diamond-like configuration, for an application different from that contemplated by the present invention, is found in an article by H. Kocak, F. Bishopp, T. Banchoff and D. Laidlaw, "Topology and Mechanics with Computer Graphics," *Advances in Applied Mathematics*, pp 1–27 (1986).

In addition to graphical displays, other information may be displayed on the display screen to assist the viewer. For example, color information may be displayed in digital form to inform the user which colors are being used on the display screen. Data information may also be digitally displayed, for example, the different percentages of data events having a particular color. In this respect, the user may be informed that a certain percentage of all data events are blue, red, green, etc. The number of dots appearing on any data field may be digitally displayed, as well as the relative position of the cursor with respect to the 128 × 128 array of a particular data field.

Another feature of the present invention is the ability to store the coordinates of the boundaries of a region of any field. Storage may be manually directed or by automatic direction in connection with the microprocessor employed with screens of the present invention. The stored coordinates may be used for subsequent analysis or for sorting subsequent samples.

Thus, the present invention provides a method for analyzing multi-parameter data, particularly flow cytometric data. The versatility of the present invention allows the user to conduct an analysis or refinement of data which was previously obtained and stored in memory. For the analysis of flow cytometric data, the instant invention provides a versatile and valuable tool particularly to immunologists, hematologists, researchers and the like who need to discriminate the different features or characteristics of complex cell samples. The instant invention gives the user the opportunity to rapidly and conveniently make such cell discriminations so that the data refining techniques are superior to other available cellular analysis procedures.

What is claimed is:

1. A method for analyzing multi-parameter, cell related data comprising:

displaying a plurality of data fields on a screen for viewing by a user, each data field defined by two axes representing two parameters relating to characteristic of cells, at least one parameter of one of said data fields being different from the parameters of the remaining data fields so that at least three different parameters of cells are represented in the plurality of data fields;

applying a position variable cursor to one of said data fields and creating a region of data events within said one data field by use of said cursor;

linking the data events in said region with corresponding data events defined by different parameters in the remaining data fields on the screen; and visually differentiating the displayed data events in the remaining data fields corresponding to the events in said created region of said one data field so that the user may identify the linked data events on all of said two-parameter data fields which correspond with each other.

2. The method of claim 1 wherein said displaying step includes displaying data fields in which four different parameters of cells are represented in the plurality of data fields.

3. The method of claim 2 wherein said four different parameters are displayed in six different two-parameter data fields on said screen.

4. The method of claim 1 wherein said displaying step includes displaying data fields simultaneously on a plurality of screens.

5. The method of claim 1 wherein said displaying step includes displaying data fields representing different parameters obtained in conjunction with cells passing through a flow cytometry instrument.

6. The method of claim 1 wherein said data fields are dot plots.

7. The method of claim 1 wherein at least one of said data fields is a histogram.

8. The method of claim 1 wherein said creating step includes using said cursor to trace a region and form an enclosure of data events.

9. The method of claim 1 wherein said creating step includes using said cursor as a brush to paint over data events on said one data field so that all such painted events are included in the region.

10. The method of claim 1 wherein said creating step includes using said cursor as a variable size box in which all data events falling within the boundaries of the box are in the region.

11. The method of claim 1 wherein said applying step includes moving the cursor on the data field by manual manipulation of a mouse which is electrically connected to said cursor and wherein the cursor is position-sensitive depending upon the position of the mouse.

12. The method of claim 1 wherein said linking step includes electrically accessing all the data events in said region and directing a signal to each remaining data field to identify each such data event defined by the two different parameters in each such remaining data field.

13. The method of claim 12 wherein said accessing step includes using a linked listing of multi-parameter data stored in memory so that each data event found in the region of said one data field may be correspondingly located in the remaining data fields but identified by the different parameters thereof.

14. The method of claim 1 wherein the differentiating step includes causing the data events in the region of said one data field and the corresponding data events in the remaining data fields to have a brightness on the screen different from data events not included within said region.

15. The method of claim 1 wherein the differentiating step includes causing the data events in the region of said one data field and the corresponding data events in the remaining data fields to intermittently blink.

16. The method of claim 1 wherein the differentiating step includes causing the data events in the region of said one data field and the corresponding data events in the remaining data fields to have a color different from data events not included in said region.

17. The method of claim 16 wherein the step of differentiating the data events includes using the cursor to adjust the size of the colored region to a larger or smaller state after the original color region has been created.

18. The method of claim 1 which further includes creating a plurality of regions of data events on said one data field and linking the data events in each respective region with corresponding data events in the remaining data fields on the screen.

19. The method of claim 18 wherein the differentiating step includes causing the data events in each region of said one data field and the corresponding data events in the remaining data fields to have a color different from each other and from data events not included in any of the regions.

20. The method of claim 19 wherein the differentiating step includes causing the colors of the different regions to overlap each other.

21. The method of claim 19 wherein the step of differentiating the data events includes eliminating all or portions of the color of any region after the original colored region has been created.

22. The method of claim 1 wherein the step of creating a region of data events on said one data field further includes using the cursor to adjust the size of the region to a larger or smaller state after the original region has been created.

23. The method of claim 1 wherein said applying step includes selectively and interchangeably applying the cursor to any other of said data fields after said cursor has been applied to said one of the data fields.

24. The method of claim 1 wherein the differentiating step includes distinguishing different types of cells.

25. The method of claim 24 wherein the differentiating step includes distinguishing different subpopulations of a type of cells.

26. The method of claim 1 further including storing coordinates of the boundaries of said region for subsequent access.

27. A method for analyzing multi-parameter data obtained by flow cytometric procedures comprising:
displaying particle-related data in a plurality of separate, two-parameter data fields on a screen for viewing by a user;
applying a position variable cursor to any two-parameter data field and creating a region within said data field by use of said cursor;
linking said region to all data events within said region;
locating data events on all other two-parameter data fields on the screen which correspond to the linked data events; and
visually differentiating all linked and corresponding events so that the user may readily identify all such data events.

28. A method for analyzing multi-parameter data comprising:
displaying data in a plurality of separate, two-parameter data fields on a screen for viewing by a user;
applying a position variable cursor to any two-parameter data field and creating a region within said data field by use of said cursor;
linking said region to all data events within said region;
locating data events on all other two-parameter data fields being displayed which correspond to the linked data events; and
visually differentiating all linked and corresponding events so that the user may readily identify all such data events.

29. The method of claim 28 wherein said displaying step includes displaying data including events which have been obtained from multiple sources.

30. A method for analyzing data to determine one or more characteristics of cells comprising:
displaying a plurality of two-parameter data fields on a screen for viewing by a user, said fields representing different displays of different parameters relating to characteristics of cells;
applying a position-variable cursor to one of said data fields and moving said cursor to enclose selective data events in a defined region;
linking the data events in said region and located corresponding events defined by different parameters in the remaining data fields on the screen by accessing a linked listing of multi-parameter data related to said cells stored in memory so that each data event falling in said region is correspondingly located in the remaining data fields, but identified by the different parameters thereof; and
visually differentiating the data events in the remaining data fields corresponding to the events in said defined region by causing all the differentiated data events to have a color different from data events not included in said region so that the user may identify the data events on all of said two-parameter data fields which correspond with each other for purposes of cellular analysis.

* * * * *